United States Patent [19]

Bauer et al.

[11] 4,163,759

[45] Aug. 7, 1979

[54] PROCESS FOR PREPARING AROMATIC HYDROXYALDEHYDES

[75] Inventors: Kurt Bauer; Werner Steuer, both of Holzminden, Fed. Rep. of Germany

[73] Assignee: Haarmann & Reimer Gesellschaft mit beschrankter Haftung, Holzminden, Fed. Rep. of Germany

[21] Appl. No.: 795,359

[22] Filed: May 9, 1977

Related U.S. Application Data

[63] Continuation of Ser. No. 234,653, Mar. 14, 1972, abandoned.

[30] Foreign Application Priority Data

Mar. 31, 1971 [DE] Fed. Rep. of Germany ....... 2115551

[51] Int. Cl.$^2$ .............................................. C07C 45/18
[52] U.S. Cl. .............................. 260/600 A; 260/600 R
[58] Field of Search ........................ 260/600 A, 600 R

[56] References Cited

U.S. PATENT DOCUMENTS

| 1,536,732 | 5/1925 | Spengler et al. ................ 260/600 A |
| 2,199,748 | 5/1940 | Mather et al. ................... 260/600 A |
| 2,640,083 | 5/1953 | Kamlet ............................. 260/600 A |

FOREIGN PATENT DOCUMENTS 445263  3/1936  United Kingdom ................ 260/600 A

*Primary Examiner*—Bernard Helfin
*Attorney, Agent, or Firm*—Sprung, Felfe, Horn, Lynch & Kramer

[57] ABSTRACT

Aromatic hydroxy aldehydes are prepared by the simultaneous oxidation and decarboxylation of hydroxy aryl glycolic acids by reacting same with oxidizing agents in aqueous-acid medium.

12 Claims, No Drawings

PROCESS FOR PREPARING AROMATIC HYDROXYALDEHYDES

This is a continuation of Application Ser. No. 234,653, filed Mar. 14, 1972, now abandoned.

This invention relates to a process for the production of aromatic hydroxyaldehydes.

SUMMARY

We have found that aromatic hydroxyaldehydes can be obtained from hydroxy aryl glycolic acids in aqueous-acid medium by using oxidizing agents.

DESCRIPTION

The aromatic glycolic acids used as starting materials in the process according to the invention can contain the hydroxy group in the aromatic radical in the 2-, 3- or 4-position. In addition, they can also contain several hydroxy groups and other substituents, such as for example alkoxy groups, halogen atoms, preferably chlorine or bromine, or alkyl radicals preferably having up to 6 carbon atoms. The following are examples of compounds such as these: 4-hydroxy phenylglycolic acid, 4-hydroxy-3-methoxyphenylglycolic acid, 4-hydroxy-3-ethoxyphenylglycolic acid, 4-hydroxy-2-methoxyphenyl glycolic acid, 4-hydroxy-3,5-dimethoxyphenylglycolic acid, 4-hydroxy-2-chlorophenylglycolic acid, 4-hydroxy-3-chlorophenyl glycolic acid, 4-hydroxy-3,5-dichlorophenylglycolic acid, 4-hydroxy-3-bromophenylglycolic acid, 4-hydroxy-3-methylphenylglycolic acid, 4-hydroxy-3,5-dimethyl phenylglycolic acid, 4-hydroxy-3,5-diethyl phenylglycolic acid, 4-hydroxy-3,5-di-tert.-butylphenylglycolic acid, 3-hydroxyphenylglycolic acid, 3-hydroxy-4-methoxyphenylglycolic acid, 3-hydroxy-4-chlorophenylglycolic acid, 3-hydroxy-4-methylphenyl glycolic acid, 2-hydroxyphenyl glycolic acid, 2-hydroxy-4-methoxy phenylglycolic acid, 2-hydroxy-4-methylphenylglycolic acid, 3,4-dihydroxyphenylglycolic acid, 4-hydroxy-2,3-benzophenylglycolic acid or 2-hydroxy-5,6-benzophenylglycolic acid or α-naphthyl glycolic acid.

4-hydroxyphenylglycolic acid, 4-hydroxy-3-methoxyphenyl glycolic acid and 4-hydroxy-3-ethoxyphenylglycolic acid are particularly preferred for the process according to the invention.

The aforementioned compounds can be obtained for example by reacting glyoxylic acid with the corresponding phenol.

The aromatic glycolic acids do not necessarily have to be used in pure form for the reaction, instead they can be used in the form in which they are produced for the process according to the invention.

Examples of oxidising agents in the aforementioned range include reducible metal salts such as, for example, copper (II) salts, mercury (II) salts, iron (III) salts, nickel (III) salts, cobalt (III) salts, chromium (VI) salts, lead (IV) salts, cerium (IV) salts, iridium (IV) salts and palladium (II) salts, also alkali metal halogenates such as for example alkali metal chlorates, alkali metal bromates, alkali metal iodates or alkali metal nitrates.

Copper (II) salts, mercury (II) salts, iron (III) salts, nickel (III) salts, cobalt (III) salts or alkali chlorates are preferably used. Copper (II) sulphate, copper (II) chloride, mercury (II) acetate, iron (III) chloride, iron (III) sulphate, nickel (III) phosphate, cobalt (III) chloride, potassium chlorate or sodium chlorate are particularly preferred.

For reaction with the hydroxyarylglycolic acid in the process according to the invention, the oxidising agent is used in an equivalent quantity or in an excess of, for example, up to 5 equivalents, and preferably in an equivalent quantity or in an excess of up to 2 equivalents.

The aforementioned reducible metal salts can of course also be used in admixture with one another. It has proved to be of advantage to use for example a mixture of an alkali metal halogenate, preferably sodium chlorate, with one or more of the aforementioned metal salts, preferably iron chloride or iron sulphates, the alkali metal chlorate being used as the main constituent of the mixture.

The reducible metal salts can of course also be produced in situ in a redox system during the reaction, for example by using a mixture of sodium chlorate and iron sulphate.

Oxidising agents with redox potentials in the range from $E_0 = +0.17$ volt to $E_0 = +1.84$ volts, are particularly preferred for the process according to the invention.

In one particular embodiment of the process the reaction in aqueous-acid solution is carried out catalytically using oxygen as the oxidising agent. Palladium or platinum is preferably used as the catalyst.

In another preferred embodiment of the process according to the invention, the reaction in aqueous-acid solution can of course also be carried out by anodic oxidation instead of using the chemical oxidising agents referred to in respect of the claimed potential range.

The process according to the invention is carried out in acid medium, preferably at pH-values of from 0 to 5 and more preferably at pH-value of from 0.3 to 3. In general, there is no need for the separate addition of acid because the hydroxy arylglycolic acids used show sufficient inherent acidity in aqueous medium and since, in addition, in adequate quantity of acid, such as for example hydrochloric acid or sulphuric acid, is in many cases liberated during oxidation. If nevertheless necessary, the pH-value can be adjusted by adding a suitable quantity of a mineral acid, for example semi-concentrated sulphuric acid.

The hydroxyaromatic glycolic acids which are readily soluble in water can be quickly and almost quantitatively oxidised into the corresponding aromatic hydroxy aldehydes by these oxidising agents in acid, homogeneous aqueous solution either at room temperature or at elevated temperature, for example at temperatures of up to 150° C., preferably at temperatures of from 50° to 100° C., the reaction being accompanied by the elimination of carbon dioxide.

Acid-sensitive and oxidation-sensitive aldehydes, such as vanillin and ethyl vanillin, can be extracted from the acid oxidation solution in the presence of a solvent immiscible with water by which the corresponding glycolic acids are taken up to a very limited extent only, for example benzene and toluene, and isolated from the extracts in the usual way.

The acid oxidation solution can be regenerated either electrochemically or by oxidation with atmospheric oxygen or other suitable oxidising agents.

Surprisingly, no condensation products are formed despite the fact that the process is carried out in acid medium.

The compounds according to the invention can be used for example as flavourings and as odorants.

The general suitablility of the process according to the invention for producing aromatic hydroxy aldehydes is illustrated in the following Examples:

EXAMPLE 1

10 g of 4-hydroxy-3-methoxyphenylglycolic acid (molecular weight 198) are dissolved in 100 g of water, and 82 g of an aqueous 20% $FeCl_3$-solution are added over a period of 20 to 30 minutes at 75° to 80° C., thus initiating a vigorous evolution of carbon dioxide which abates after another 30 minutes. The reaction takes place at a pH-value of from 2 to 0.8. Most of the 4-hydroxy-3-methoxy benzaldehyde formed completely crystallises out of the acid oxidation solution on cooling. The 4-hydroxy-3-methoxybenzaldehyde can be completely extracted from the oxidation solution with benzene or toluene. The extract is washed with a little water, after which the solvent is distilled off until the 4-hydroxy-3-methoxybenzaldehyde can be precipitated from the mother liquor in crystalline form with cyclohexane or with light petrol.

Yield: 7.2 g of 4-hydroxy-3-methoxybenzaldehyde, corresponding to 95% of the theoretical yield.

Analysis: M.p. 79° to 80° C., pure 4-hydroxy-3-methoxybenzaldehyde according to the CO-number and a thin-layer chromatogram (the CO-number is obtained from aldehyde determination by volumetric analysis in accordance with the oximation method).

EXAMPLE 2

10 g of 4-hydroxy-3-methoxyphenylglycolic acid are dissolved in 100 g of water, and 86 g of an aqueous 20% solution of $CuCl_2.2 H_2O$ are added over a period of 30 minutes at 100° C., initiating a moderate evolution of carbon dioxide which abates after another 2 hours at 100° C. The reaction takes place at a pH-value of 1.8 to 0.8. The acid oxidation solution is worked up as described in Example 1.

Yield: 6.8 g of 4-hydroxy-3-methoxybenzaldehyde, corresponding to 89% of the theoretical yield.

Analysis: M.p. 78° to 79° C., pure according to the CO-number and a thin-layer chromatogram.

EXAMPLE 3

Oxidation of the pure condensation product of guaiacol and glyoxylic acid (a) An acid aqueous solution of 4-hydroxy-3-methoxyphenyl glycolic acid obtained in accordance with Example 3b is heated with 2000 ml of toluene to the reflux temperature of 85° to 86° C., and 800 g of iron (III) sulphate are added in portions with stirring over a period of 1 hour, initiating a vigorous evolution of carbon dioxide. The reaction takes place at a pH-value of from 2 to 0.8. The toluene solution is separated off and the reaction mixture stirred with fresh toluene for another hour at 85° C., after which the two phases are separated again. The reaction mixture is then stirred for another hour (3rd hour) at 100° C. in the absence of toluene until the evolution of carbon dioxide abates, after which it is thoroughly extracted with toluene. The toluene extracts are worked up as in Example 1.

Yield: 265 g of 4-hydroxy-3-methoxybenzaldehyde corresponding to 86% of the theoretical (based on the guaiacol reacted in accordance with Example 3b).

Analysis: M.p. 77° to 78° C.; 97% pure according to the CO-number and a thin-layer chromatogram.

(b) Preparation of the starting material: 356 g of a 50% aqueous glyoxylic acid (2.4 mols) are neutralised at 15° to 25° C. with 1920 g of 5% sodium hydroxide solution, subsequently admixed while stirring with a solution of 372 g of guaiacol (3 mols) in 1200 g of 10% sodium hydroxide and the resulting mixture is left to stand for 36 hours at 15° to 25° C. The alkaline condensation mixture is then acidified while cooling with 50% sulphuric acid to a pH-value of from 4 to 5. 124.5 g of unreacted guaiacol are extracted from the acid solution with toluene.

EXAMPLE 4

9.3 g of 4-hydroxyphenylglycolic acid in the form of the monohydrate (molecular weight 186) are dissolved in 50 g of water, and 82 g of an aqueous 20% $FeCl_3$ solution are added over a period of 20 to 30 minutes at 75° to 80° C., initiating a vigorous evolution of carbon dioxide which stops after another 30 minutes at 100° C. The reaction takes place at a pH-value of from 2 to 0.8. Most of the 4-hydroxybenzaldehyde formed crystallises out of the acid oxidation solution on cooling to 0° C. and is filtered off under suction. The residual 4-hydroxy benzaldehyde is removed from the cold aqueous mother liquor by repeated extraction with benzene. Most of the p-hydroxybenzaldehyde is added to the benzene solution thus obtained, most of the benzene evaporated off and pure 4-hydroxybenzaldehyde precipitated in crystalline form either with light petrol or with cyclohexane.

Yield: 5.2 g of 4-hydroxybenzaldehyde, corresponding to 85% of the theoretical.

Analysis: M.P. 115° to 116° C., 100% pure according to the CO-number and a thin-layer chromatogram.

EXAMPLE 5

Oxidation of the crude condensation product of phenol and glyoxylic acid (a) 800 g of iron (III) sulphate are added in portions with stirring over a period of 60 minutes at 75° to 80° C. to an acid aqueous solution of 4-hydroxyphenylglycolic acid obtained in accordance with Example 5b, initiating a vigorous evolution of carbon dioxide which stops after another hour at 100° C. The reaction takes place at a pH-value of from 2 to 0.8. p-hydroxy benzaldehyde is recovered from the acid oxidation solution as in Example 4. Since the crude condensation product of phenol with glyoxylic acid also contains small quantities of 2-hydroxy phenylglycolic acid in addition to the 4-hydroxy-phenylglycolic acid, a little sulicylalochyde is also formed during oxidation, regaining in the mother liquor following precipitation of the 4-hydroxybenzaldehyde as in Example 4.

Yield: 197 g of 4-hydroxybenzaldehyde, corresponding to 81% of the theoretical yield, and 17 g of a mixture of 20% of 4-hydroxy benzaldehyde and 80% of salicylaldehyde, corresponding to 7% of the theoretical yield (based on the phenol reacted in accordance with Example 5b).

(b) Preparation of the starting material: 336 g of 53% aqueous glyoxylic acid (2.4 mols) are neutralised at 15° to 25° C. with 1920 g of 5% sodium hydroxide solution, subsequently mixed while stirring with a solution of 282 g of phenol (3 mols) in 1200 g of 10% sodium hydroxide solution and the resulting mixture is left standing for 36 hours at 15° to 25° C. The alkaline condensation mixture is then acidified while cooling with 50% sulphuric acid with a pH vaue of from 4 to 5, 95 g of unreacted phenol are extracted from the acid solution with benzene.

EXAMPLE 6

11.5 g of 4-hydroxy-3-ethoxyphenylglycolic acid in the form of the monohydrate (molecular weight 230) are dissolved in 100 ml of water. The acid solution (pH 2) has 100 ml of toluene poured onto it, and the mixture is heated to 75°–80° C. 56.7 g of 30% $FeCl_3$ solution are then added with stirring at this temperature over a period of 20 minutes, initiating a vigorous evolution of carbon dioxide. The mixture is then boiled under reflux (85° to 86° C.) for another 20 minutes. After the toluene phase has been separated off, the residual aqueous solution is heated to the boil, the remaining carbon dioxide being evolved over a period of 10 minutes. On completion of oxidation, the acidity of the solution has increased to pH 1. Then the solution is thoroughly extracted with toluene. The combined toluene solutions are washed with a little water, filtered and the solvent distilled off until 4-hydroxy-3-ethoxybenzaldehyde can be precipitated in crystalline form from the mother liquor either with cyclohexane or with light petrol.

Yield: 7.7 g, corresponding to 93% of the theoretical yield.

Analysis: M.p. 75° to 76° C., substantially pure 4-hydroxy-3-ethoxybenzaldehyde according to the CO-number and a thin-layer chromatogram.

EXAMPLE 7

10 g of 4-hydroxy-3-methoxyphenylglycolic acid (molecular weight 198) are dissolved in 100 g of water. The aqueous acid solution (pH 2) has 100 ml of toluene poured onto it, followed by heating with stirring to 75°–85° C. At upwards of 75° C., a solution of 0.5 g of $FeCl_3$ in 1 g of water is initially introduced, followed by the introduction over a period of 10 minutes of a solution of 2.1 g of $KClO_3$ in 38 g of water, initiating a vigorous evolution of carbon dioxide which abates after 30 minutes at 85° C. On completion of oxidation, the oxidation solution has a pH-value of approximately 1. After the toluene extract has been distilled off, the aqueous oxidation solution is heated to 95°–100° C. until the evolution of $CO_2$ has ceased which takes about 20 to 30 minutes.

Most of the 4-hydroxy-3-methoxybenzaldehyde formed completely crystallises out of the oxidation solution on cooling. The 4-hydroxy-3-methoxybenzaldehyde can be completely extracted from the oxidation solution with benzene or toluene. The extract is washed with a little water after which the solvent is distilled off until 4-hydroxy-3-methoxybenzaldehyde can be precipitated in crystalline form from the mother liquor with cyclohexane.

Yield: 5.3 g of crystallised 4-hydroxy-3-methoxybenzaldehyde. Another 1.4 g of 4-hydroxy-3-methoxybenzaldehyde are contained in 1.9 g of residue.

Total yield: 6.7 g, corresponding to 87% of the theoretical yield.

EXAMPLE 8

(a) 11.5 g of 4-hydroxy-3-ethoxyphenylglycolic acid in the form of the monohydrate (molecular weight 230) are dissolved in 100 g of water. The aqueous acid solution (pH 2) has 100 ml of toluene poured on to it, followed by heating with stirring to 75°–85° C. At upwards of 75° C., a solution of 0.5 g of $FeCl_3$ in 1 g of water is initially introduced, followed by the introduction over a period of 10 minutes of a solution of 1.82 g of $NaClO_3$ in 35 g of water, initiating a vigorous evolution of carbon dioxide which abates after 35 minutes at 85° C. On completion of oxidation, the oxidation solution has a pH-value of approximately 1. After the toluene extract has been distilled off, the aqueous oxidation solution is heated to 95°–100° C. until the evolution of carbon dioxide has stopped which takes 30 minutes.

This is followed by extraction of the oxidation solution with toluene and working up of the extract as in Example 6.

Yield: 7.4 g of 4-hydroxy-3-ethoxybenzaldehyde, corresponding to 90% of the theoretical yield.

Analysis: M.p. 75° C., substantially pure 4-hydroxy-3ethoxy benzaldehyde according to volumetric analysis and a thin-layer chromatogram.

(b) A corresponding result is obtained where an equivalent quantity of an iron sulphate is used instead of the iron chloride.

EXAMPLE 9

Oxidation of the crude condensation product of guaiacol and glyoxylic acid (a) An aqueous-acid solution of 4-hydroxy-3-methoxyphenylglycolic acid prepared in accordance with Example 9b is adjusted with 37.5 g of 60% sulphuric acid to a pH-value of from 0.8 to 0.9, heated with 931 ml of toluene to the reflux temperature of 85° to 86° C., followed by the addition in portions with stirring over a period of 1 hour of a mixture of 66 g of 10% iron (II) sulphate solution and 372 g of 5% sodium chlorate solution, initiating a vigorous evolution of carbon dioxide. On completion of oxidation, the oxidation solution has a pH-value of approximately 1. The toluene solution is separated off and the mixture stirred with fresh toluene for another hour at 85° C., after which the two phases are separated again. The mixture is then stirred for another hour (third hour) in the absence of toluene at 100° C. until the evolution of $CO_2$ has abated, after which it is thoroughly extracted with toluene. The toluene extracts are worked up as in Example 1.

Yield: 47.5 g of 4-hydroxy-3-methoxyphenylglycolic acid, corresponding to 95% to the theoretical (based on the guaiacol reacted in accordance with Example 9b).

Analysis: M.p. 77°–78° C.; approximately 95% pure according to the CO-number and a thin-layer chromatogram.

(b) Preparation of the starting material: 50 g of 50% aqueous glyoxylic acid (0.34 mol) are neutralised at 15° to 25° C. with 225 g of 7% sodium hydroxide solution, mixed while stirring with a solution of 63 g of guaiacol (0.46 mol) in 319 g of 7% sodium hydroxide solution and the resulting mixture is left standing for 36 hours at 15° to 25° C. The alkaline condensation mixture is then adjusted with 75 g of 60% sulphuric acid to a pH-value of approximately 3. 21 g of unreacted guaiacol are extracted with toluene from the acid solution.

(c) Similar results are obtained where a cobalt (II) sulphate solution or a nickel (II) sulphate solution is used as oxidising agent, instead of the iron (II) sulphate solution.

What is claimed is:

1. The process for the preparation of an aromatic hydroxyaldehyde of the formula

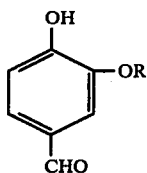

wherein

R is methyl or ethyl, which comprises condensing a phenol of the formula

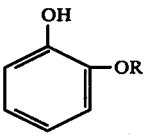

with glyoxylic acid to produce a substituted glyoxylic acid of the formula

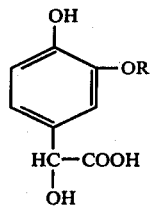

and oxidizing said substituted glyoxylic in aqueous acid at a pH at most 5 with an oxidizing agent having a redox potential in the range of from $E = +0.17$ to $+1.84$ volts wherein the oxidizing agent is potassium chlorate or sodium chlorate in admixture with copper, iron, cobalt or nickel sulphate or chloride, whereby the aromatic hydroxyaldehyde is produced in high yield based on starting phenol.

2. Process of claim 1 wherein the reaction is carried out at pH-values in the range from 0.3 to 3.

3. Process of claim 1 wherein the oxidizing agent is used either in an equivalent quantity or in an excess of up to 5 equivalents.

4. Process of claim 1 wherein the oxidation is effected at up to 100° C.

5. Process of claim 1, wherein R is methyl.

6. Process of claim 5 wherein iron sulphate and sodium chlorate is used as the oxidizing agent.

7. Process of claim 5 wherein iron chloride and potassium chlorate are used as the oxidizing agent.

8. Process of claim 5 wherein iron (III) chloride is used in the oxidizing agent.

9. Process of claim 1 wherein R is ethyl.

10. Process of claim 9 wherein iron sulphate and sodium chlorate are used as the oxidizing agent.

11. Process of claim 9 wherein iron chloride and sodium chlorate are used as the oxidizing agent.

12. Process of claim 9 wherein iron (III) chloride is used in the oxidizing agent.

* * * * *

UNITED STATES PATENT AND TRADEMARK OFFICE
CERTIFICATE OF CORRECTION

PATENT NO. : 4,163,759
DATED : August 7, 1979
INVENTOR(S) : KURT BAUER ET AL

It is certified that error appears in the above-identified patent and that said Letters Patent are hereby corrected as shown below:

| COLUMN | LINE | |
|---|---|---|
| 4 | 49 | "sulicylalochyde" should be --salicylaldehyde--. |
| 4 | 50 | "regaining" should be --remaining--. |
| 6 | 14 | "3ethoxy" should be --3-ethoxy--. |
| 6 | 45 | "to" 2nd occurr. should be --of--. |

Signed and Sealed this

Nineteenth Day of February 1980

[SEAL]

Attest:

SIDNEY A. DIAMOND

Attesting Officer    Commissioner of Patents and Trademarks